(12) United States Patent
Lee et al.

(10) Patent No.: US 6,287,314 B1
(45) Date of Patent: *Sep. 11, 2001

(54) STENT DEPLOYING CATHETER SYSTEM

(75) Inventors: Jeong S. Lee, Diamond Bar; Florencia Lim, Union City, both of CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/063,969

(22) Filed: Apr. 21, 1998

(51) Int. Cl.[7] ................................................. A61M 29/00
(52) U.S. Cl. .......................... 606/108; 606/194; 606/195
(58) Field of Search ................................ 606/108, 198, 606/195, 194, 192; 623/1, 12; 604/96, 99, 282, 913

(56) References Cited

U.S. PATENT DOCUMENTS

| | | | |
|---|---|---|---|
| 4,106,509 | 8/1978 | McWhorter | 128/349 |
| 4,265,848 | 5/1981 | Riisch | 264/130 |
| 4,315,512 | 2/1982 | Fogarty | 128/344 |
| 4,331,142 | 5/1982 | Degen | 128/207 |
| 4,463,156 | 7/1984 | McGary, Jr. et al. | 528/65 |
| 4,564,014 | 1/1986 | Fogarty et al. | 128/344 |
| 4,572,186 | 2/1986 | Gould et al. | 128/341 |
| 4,706,670 | 11/1987 | Anderson et al. | 128/344 |
| 4,762,128 | 8/1988 | Rosenbluth | 128/343 |
| 4,820,271 | 4/1989 | Deutsch | 604/99 |
| 4,950,239 | 8/1990 | Gahara et al. | 604/96 |
| 5,112,304 | 5/1992 | Barlow et al. | 604/96 |
| 5,290,306 | 3/1994 | Trotta et al. | 606/194 |
| 5,348,538 | * 9/1994 | Wang et al. | 604/96 |
| 5,358,487 | * 10/1994 | Miller | 604/96 |
| 5,366,472 | 11/1994 | Hillstead | 606/194 |
| 5,409,495 | 4/1995 | Osborn | 606/108 |
| 5,415,635 | 5/1995 | Bagaoisan et al. | 604/96 |
| 5,439,443 | 8/1995 | Miyata et al. | 604/96 |
| 5,443,495 | 8/1995 | Buscemi et al. | 623/1 |

(List continued on next page.)

FOREIGN PATENT DOCUMENTS

| | | |
|---|---|---|
| 0 210 061 A2 | 1/1987 | (EP) . |
| 357 562 | 3/1990 | (EP) . |
| 0 540 858 | 5/1993 | (EP) . |
| 0 553 960 | 8/1993 | (EP) . |
| 592 885 | 4/1994 | (EP) . |
| 745 395 | 12/1996 | (EP) . |
| 0 778 037 A1 | 6/1997 | (EP) . |
| WO 95/23619 | 9/1995 | (WO) . |
| WO 96/37240 | 11/1996 | (WO) . |
| WO 98/05377 | 2/1998 | (WO) . |

* cited by examiner

*Primary Examiner*—Pedro Philogene
(74) *Attorney, Agent, or Firm*—Heller Ehrman White & McAuliffe

(57) ABSTRACT

An intravascular catheter system for properly implanting a stent in a body lumen generally comprising a catheter having an elongated shaft with an inflatable balloon formed of compliant material and a stent mounted on the working length of the balloon. The balloon material is compliant within the working range of the balloon to provide substantial radial expansion. The wingless radially expansive balloon expands in a uniform manner, thereby producing uniform expansion and implantation of the stent.

22 Claims, 2 Drawing Sheets

U.S. PATENT DOCUMENTS

| | | | | |
|---|---|---|---|---|
| 5,458,605 | * | 10/1995 | Klemm | 606/108 |
| 5,470,313 | | 11/1995 | Crocker et al. | 604/96 |
| 5,492,532 | | 2/1996 | Ryan et al. | 604/96 |
| 5,500,180 | | 3/1996 | Anderson et al. | 264/532 |
| 5,500,181 | | 3/1996 | Wang et al. | 264/532 |
| 5,556,383 | | 9/1996 | Wang et al. | 604/96 |
| 5,628,754 | * | 5/1997 | Shevlin et al. | 606/108 |
| 5,643,278 | * | 7/1997 | Wijay | 606/108 |
| 5,645,560 | | 7/1997 | Crocker et al. | 606/192 |
| 5,669,880 | * | 9/1997 | Solar | 604/96 |
| 5,707,354 | | 1/1998 | Salmon et al. | 604/96 |
| 5,738,901 | | 4/1998 | Vickerman et al. | |
| 5,743,874 | * | 4/1998 | Fischell et al. | 604/96 |
| 5,749,851 | * | 5/1998 | Wang | 604/96 |
| 5,752,934 | | 5/1998 | Campbell et al. | 604/96 |
| 5,766,203 | * | 6/1998 | Imran et al. | 606/198 |
| 5,769,817 | * | 6/1998 | Burgmeier | 604/96 |
| 5,772,669 | * | 6/1998 | Vrba | 606/108 |
| 5,776,140 | * | 7/1998 | Cottone | 606/108 |
| 5,792,144 | * | 8/1998 | Fischell et al. | 606/108 |
| 5,792,300 | | 8/1998 | Querns et al. | |
| 5,833,706 | * | 11/1998 | St. Germain et al. | 606/194 |
| 5,868,704 | | 2/1999 | Campbell et al. | 604/96 |

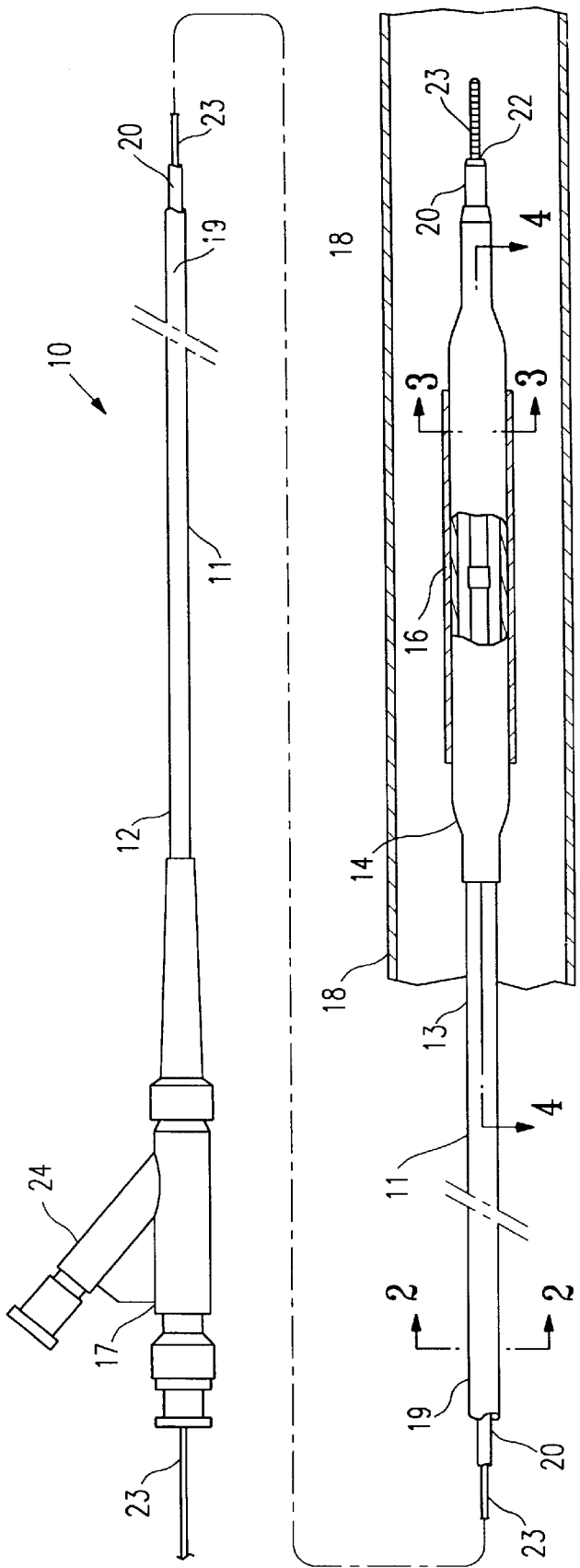
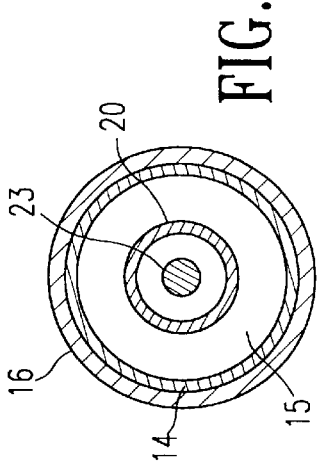
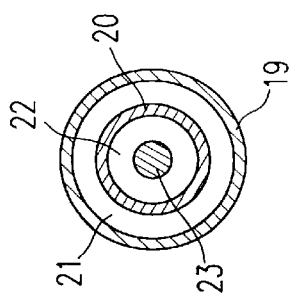
FIG. 1
FIG. 2
FIG. 3

STENT DEPLOYING CATHETER SYSTEM

BACKGROUND OF THE INVENTION

The invention relates to the field of intravascular stent deploying catheters, and more particularly to a catheter balloon formed of compliant material with a uniform radial expansion that provides for improved stent deployment.

In percutaneous transluminal coronary angioplasty (PTCA) procedures a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to open a stenosed vessel, and strengthen the dilated area by remaining inside the vessel.

In conventional stent deploying balloon catheters, the balloon is made of essentially non-compliant material, such as nylon or polyethyleneterephthalate (PET). Such non-compliant material exhibits little expansion in response to increasing levels of inflation pressure. Because the non-compliant material has a limited ability to expand, the uninflated balloon must be made sufficiently large that, when inflated, the balloon has sufficient working diameter to compress the stenosis and open the patient's passageway. However, a large profile non-compliant balloon can make the catheter difficult to advance through the patient's narrow vasculature because, in a uninflated condition, such balloons form flat or pancake shape wings which extend radially outward. Consequently, the wings of an uninflated balloon are typically folded into a low profile configuration for introduction and advancement through the vessel. The wings are again produced upon deflation of the balloon following stent deployment within the patient. These wings on the deflated balloon are undesirable because they result in an increased balloon profile which can complicate withdrawing the catheter after stent deployment.

Although stents have been used effectively for some time, the effectiveness of a stent can be diminished if it is not properly implanted within the vessel. For example, expansion of a balloon folded into a low profile configuration for introduction into the patient, can cause nonuniform expansion of a stent mounted on the balloon. The nonuniform expansion of conventional designs has resulted in the use of an elastic sleeve around the balloon and under the stent to distribute force from the expanding folded balloon to the stent uniformly, see for example U.S. Pat. No. 5,409,495 (Osborn), which is incorporated herein by reference. However, such sleeves may fail to completely prevent the nonuniform expansion of the stent, they increase the deflated profile upon insertion into the patient, and they complicate the assembly of the stent onto the balloon. Additionally, the final location of the implanted stent in the body lumen may be beyond the physician's control where longitudinal growth of the stent deploying balloon causes the stent's position on the balloon to shift during deployment. As the balloon's axial length grows during inflation, the stent may shift position along the length of the balloon, and the stent may be implanted upstream or downstream of the desired location in the body lumen. Thus, balloons which have a large amount of longitudinal growth during inflation provide inadequate control over the location of the implanted stent.

Therefore, what has been needed is a stent delivery system in which the stent is more uniformly expanded and implanted into the patient. The present invention satisfies these and other needs.

SUMMARY OF THE INVENTION

The invention is directed to a stent delivery system with a stent deploying balloon formed of compliant material that uniformly expands the stent to properly implant the stent within the patient's body lumen.

The stent delivery system of the invention generally comprises a catheter having an elongated shaft with an inflatable balloon on a distal portion of the catheter and a stent disposed about the working length of the balloon. The balloon is formed of material compliant at least within a working range of the balloon, and which therefore provides for substantially uniform radial expansion within the working range. The compliant balloon material therefore expands substantially elastically when pressurized at least within the pressure range disclosed herein for use in inflating the stent deploying balloon of the invention. The compliant balloon material will generally be an highly elastic material. The term "compliant" as used herein refers to thermosetting and thermoplastic polymers which exhibit substantial stretching upon the application of tensile force. Additionally, compliant balloons transmit a greater portion of applied pressure before rupturing than non-compliant balloons. Suitable compliant balloon materials include, but are not limited to, elastomeric materials, such as elastomeric varieties of latex, silicone, polyurethane, polyolefin elastomers, such as polyethylene, flexible polyvinyl chloride (PVC), ethylene vinyl acetate (EVA), ethylene methylacrylate (EMA), ethylene ethylacrylate (EEA), styrene butadiene styrene (SBS), and ethylene propylene diene rubber (EPDM). The presently preferred compliant material has an elongation at failure at room temperature of at least about 250% to at least about 500%, preferably about 300% to about 400%, and a Shore durometer of about 50A to about 75D, preferably about 60A to about 65D.

When the stent delivery balloon of the invention is pressurized, the balloon expands radially in a uniform manner to a working diameter. Because the balloon expands uniformly without unwrapping wings, it will uniformly expand a stent mounted on the balloon. The uninflated balloon does not require folding into a low profile configuration for insertion into the patient or the use of elastomeric sleeves used with conventional stent deploying balloons made from relatively non-compliant material. Similarly, the balloon of the invention should have a substantial elastic recoil so that it deflates into a smaller diameter with little or no wings. The undesirable flat or pancake shape wings which form when conventional stent deploying balloons are deflated are thus avoided. Additionally, minimal axial growth of the balloons during inflation provides improved control over the placement of the implanted stent in the body lumen. The compliant balloon results in improved abrasion and puncture resistance relative to the conventional non-compliant stent deploying balloons at least in part because there is little or no movement between the balloon and stent when the balloon expands radially. Moreover, due to the compliant nature of the balloon, there is a more highly efficient transfer of force to the stent than with the high pressure non-compliant conventional balloons which expend much expansive force to overcome rigidity (non-compliance) and to size the stent.

These and other advantages of the invention will become more apparent from the following detailed description of the invention and the accompanying exemplary drawings.

BRIEF DESCRIPTION OF THE DRAWINGS

FIG. 1 is an elevational view partially in section of the catheter system of the invention showing the balloon in an unexpanded state.

FIG. 2 is a transverse cross sectional view of the catheter system of FIG. 1 taken along lines 2—2.

FIG. 3 is a transverse cross sectional view of the catheter system of FIG. 1 taken along lines 3—3.

DETAILED DESCRIPTION OF THE INVENTION

Figure 4:
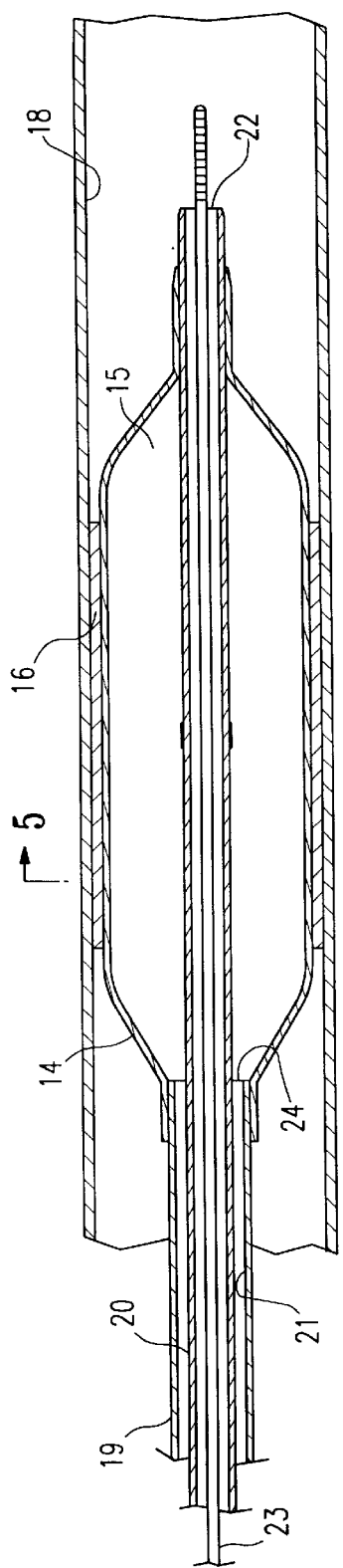
FIG. 4 is an elevational view partially in section of the distal section of the catheter system of the invention as shown in FIG. 1 depicting the balloon and stent expanded.

FIG. 1 illustrates an intravascular catheter system for implanting a stent in a body lumen. The catheter system of the invention generally includes a catheter 10 having an elongated catheter shaft 11 having a proximal 12 and distal 13 section, a radially expansive inflatable balloon 14 on the distal section 13 of the catheter shaft 11, a stent 16 mounted on the balloon 14, and an adapter 17 mounted on the proximal section 12 of shaft 11.

Figure 5:
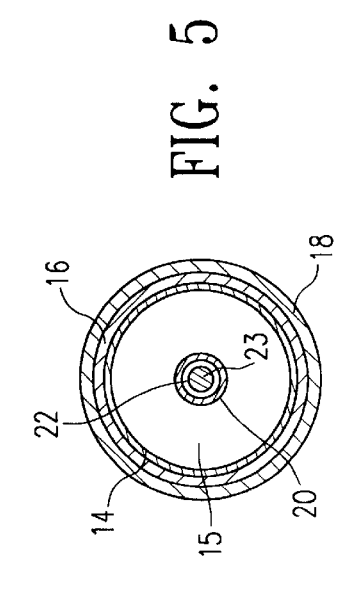
FIG. 5 is a transverse cross sectional view of the expanded balloon and stent of FIG. 4 taken. along lines 5—5.

In FIG. 1, the catheter system is illustrated within a patient's body lumen 18, with the stent 16 in an unexpanded state prior to expansion of the balloon 14. The inflatable balloon 14 is formed of radially expansive material that is compliant within the working range of the balloon. As best illustrated in FIG. 3, the compliant balloon is essentially wingless and does not require folding into a low profile configuration for insertion into the patient. FIG. 4 illustrates the balloon in an expanded state during stent deployment. FIG. 5 illustrates a transverse cross section of the balloon illustrated in FIG. 4 taken along lines 5—5.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

The balloon 14 may be formed of any compliant material, and includes thermoplastic and thermosetting polymers. The presently preferred compliant polymeric materials providing a wingless balloon with substantially elastic recoil during deflation include polyurethanes such as TECOTHANE from Thermedics. TECOTHANE is a thermoplastic, aromatic, polyether polyurethane synthesized from methylene disocyanate (MDI), polytetramethylene ether glycol (PTMEG) and 1,4 butanediol chain extender. TECOTHANE grade 1065D is presently preferred, and has a Shore durometer of 65D, an elongation at break of about 300%, and a high tensile strength at yield of about 10,000 psi. However, other suitable grades may be used, including TECOTHANE 1075D, having a Shore D of 75. Balloons produced from the TECOTHANE materials are particularly preferred because the axial growth of the balloon during inflation in minimized, and the axial and radial size of the balloon deflates to the original preinflation size following inflation and deflation of the balloon. Thus, inflation produces little or no axial or radial growth, so that the deflated balloons elastically recoil to the preinflation size. Other suitable compliant polymeric materials which deflate so that at least the radial size of the balloon returns to the original preinflation radial size, and which therefore have a substantially elastic recoil after deflation, include ENGAGE from DuPont Dow Elastomers (an ethylene alpha-olefin polymer) and EXACT, available from Exxon Chemical, both of which are thermoplastic polymers and are believed to be polyolefin elastomers produced from metallocene catalysts. Other suitable compliant materials include, but are not limited to, elastomeric silicones, latexes, and urethanes. The type of compliant material may be chosen to provide compatibility with the catheter shaft material, to thereby facilitate bonding of the balloon to the catheter.

The stent deploying balloon of the invention can be produced by conventional techniques for producing catheter inflatable members, and may be preformed by stretching a straight tube formed of the compliant material or formed in situ after attachment to the catheter shaft. Because the compliant material provides substantial radial expansion, the balloon need not be preformed, unlike non-compliant stent deploying balloons, so that production of the compliant balloon catheter of the invention is simplified relative to conventional non-compliant balloon catheters.

FIG. 2, showing a transverse cross section of the catheter shaft 11, illustrates the guidewire receiving lumen 22 and inflation lumen 21. The balloon 14 can be inflated by radiopaque fluid from an inflation port 24, from inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

The compliant balloon has sufficient strength to withstand the inflation pressures needed to inflate the balloon and expand the stent mounted thereon. The burst pressure of the compliant balloon (about 3.0 mm) is about 10 atm to about 15 atm, and the tensile strength of an American Standard Testing Method (ASTM) "dog-bone" sample cut from a compression molded sheet of material is about 3000 psi to about 7500 psi. The hoop strength, e.g. the product of the burst pressure and the balloon diameter, divided by two times the balloon wall thickness, of a 3.0 mm balloon of the invention is about 10,000 psi to about 20,000 psi. The hoop strength of a 2.5 mm balloon formed from TECOTHANE 1065D is about 18,000 psi. The inflation pressure needed to expand a stent varies depending on the balloon material and stent material and design, but is generally about 6 atm to about 8 atm.

The compliant material may be cross linked or uncrosslinked, depending upon the balloon material and characteristics required for a particular application. The presently preferred polyurethane balloon materials are not crosslinked. However, other suitable materials, such as the polyolefinic polymers ENGAGE and EXACT, are preferably crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent to an undesirably large diameter.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 1.5 cm to about 3.0 cm, and is typically about 2.0 cm. In an uninflated or deflated state the balloon diameter is generally about 0.015 in (0.4 mm) to about 0.08 in (2 mm), and is typically about 0.037 in (1 mm), and the wall thickness is generally about 0.004 in (0.1 mm) to about 0.016 in (0.4 mm), and is typically about 0.008 in (0.2 mm). In an expanded state, the balloon diameter is generally about 0.06 in (1.5 mm) to about 0.18 in (4.5 mm), and the wall thickness is about 0.0005 in (0.012 mm) to about 0.0025 in (0.06 mm).

Various designs for dilatation catheters well known in the art may be used in the catheter system of the invention. For example, conventional over-the-wire dilatation catheters for angioplasty usually include a guidewire receiving lumen extending the length of the catheter shaft from a guidewire port in the proximal end of the shaft. Rapid exchange dilatation catheters generally include a short guidewire lumen extending to the distal end of the shaft from a guidewire port located distal to the proximal end of the shaft.

Figure 6:
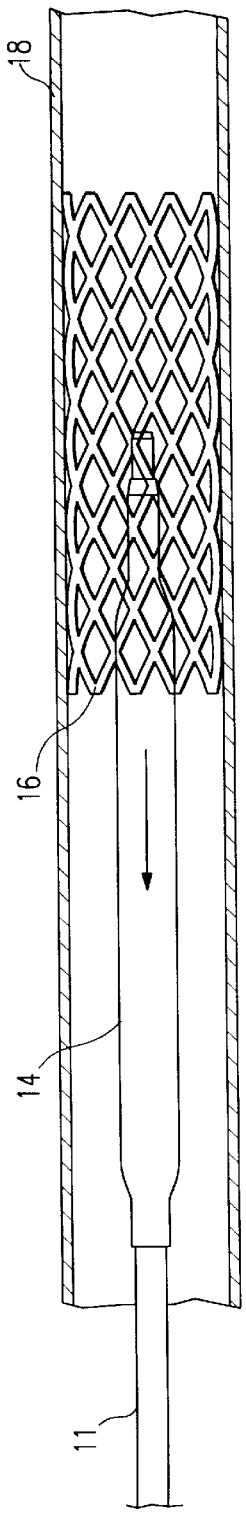
FIG. 6 illustrates the catheter system shown in FIG. 1, depicting the balloon in a deflated state and the stent implanted within the patient's lumen.

When delivering a stent into a patient, the catheter 10 is inserted into a patient's vasculature to the desired location which is shown in FIGS. 1 and 4 as a dilated stenotic region, and inflation fluid is delivered through the inflation lumen 21 to the compliant balloon 14 through the inflation port 24. Because of the balloon's compliant material, it expands radially. Longitudinal growth can be prevented by the inner tubular member 20 or by stretching or axial orientation during processing. Consequently, the stent 16 mounted on the balloon expands uniformly. When the inflation fluid is removed, the balloon 14 retracts to a wingless shape from elastic recoil to allow the catheter to be withdrawn The stent remains in place in the patient's body lumen, as illustrated in FIG. 6 showing the deflated balloon 14 and expanded stent 16 within the body lumen 18. The stent 16 may be any of a variety of stent materials and forms designed to be implanted by an expanding member, see for example U.S. Pat. Nos. 5,514,154 (Lau et al.) and 5,443,500 (Sigwart), incorporated by reference. For example, the stent material may be stainless steel, a NiTi alloy, a Co—Cr—Mo containing alloy such as MP-35N, a plastic material, or various other materials. The stent has a smaller diameter for insertion and advancement into the patient's lumen which may be formed by contracting the stent or by folding at least a portion of the stent into a wrapped configuration.

EXAMPLE

TECOTHANE 1065D was used to prepare balloon tubing having a mean ID of about 0.0195 inch (0.5 mm) and a mean OD of about 0.0355 inch (0.9 mm), and the balloon tubing was used to prepared balloons having an OD of about 2.5 mm. The mean balloon OD was about 0.110 inch (2.8 mm), and mean dual wall thickness was about 0.0015 inch (0.038 mm). The mean rupture pressure was about 238 psi, and the mean hoop strength was about 18,000 psi. Radial (OD) and axial (length) compliance measurements were made on the unrestrained balloons. The term unrestrained refers to a balloon with one end attached to an inflation medium source and the other end clamped shut, as opposed to a balloon with proximal and distal ends secured to a catheter shaft. The balloons have a substantially uniform radial expansion, as illustrated in Table 1, which lists the average ballon OD for the unruptured balloons, at a given inflation pressure, for five balloons tested. The balloons also have minimal axial growth during inflation, as illustrated in Table 2, which lists the average working length for the unruptured balloons, of five balloons tested, at a given inflation pressure. The axial growth, to rupture, of the balloons is about 32% to about 35% of the original, uninflated 20 mm working length. Moreover, this axial lengthening would be expected to be less in a secured balloon having proximal and distal ends secured to a catheter shaft.

TABLE 1

| Inflation Pressure (PSI) | Average Balloon OD (MM) |
|---|---|
| 30 | 2.476 |
| 45 | 2.743 |
| 60 | 2.917 |
| 75 | 3.044 |

TABLE 1-continued

| Inflation Pressure (PSI) | Average Balloon OD (MM) |
|---|---|
| 90 | 3.148 |
| 105 | 3.239 |
| 120 | 3.324 |
| 135 | 3.405 |
| 150 | 3.482 |
| 165 | 3.560 |
| 180 | 3.634 |
| 195 | 3.709 |
| 210 | 3.776 |
| 225 | 3.853 |
| 240 | 3.996 |
| 255 | 4.089 |

TABLE 2

| Inflation Pressure (PSI) | Average Balloon Working Length (MM) |
|---|---|
| 30 | 20.6 |
| 45 | 21.4 |
| 60 | 22.4 |
| 75 | 22.8 |
| 90 | 23.6 |
| 105 | 24.1 |
| 120 | 24.5 |
| 135 | 24.9 |
| 150 | 25.4 |
| 165 | 25.6 |
| 180 | 26.t |
| 195 | 26.5 |
| 210 | 26.5 |
| 225 | 26.75 |
| 240 | 27 |
| 255 | 27 |

It will be apparent from the foregoing that, while particular forms of the invention have been illustrated and described, various modifications can be made without departing from the spirit and scope of the invention. For example, while the balloon catheter illustrated in FIG. 1 has inner and outer tubular members with independent lumens, a single tubular membered shaft having two lumens therein may also be used. Other modifications may be made without departing from the scope of the invention.

What is claimed is:

1. An intravascular catheter system for implanting a stent in a patient's body, comprising:
   a) a catheter having an elongated shaft with proximal and distal ends and an inflation lumen extending within at least a portion of a distal shaft section to a location spaced proximally from the distal end;
   b) an essentially wingless radially expansive uninflated compliant balloon formed of polymeric material, mounted on the distal section of the catheter shaft, with an interior chamber in fluid communication with the inflation lumen; and
   c) an expandable stent disposed about and mounted onto the essentially wingless uninflated balloon so that radial expansion of the balloon expands the stent mounted thereon and implants the stent in the body.

2. The intravascular catheter system of claim 1 wherein the polymeric material has an elongation at failure at room temperature of at least about 300%.

3. The intravascular catheter system of claim 1 wherein the polymeric material has an elongation at failure at room temperature of at least about 500%.

4. The intravascular catheter system of claim 1 wherein the polymeric material has a Shore durometer hardness of about 50A to about 75D.

5. The intravascular catheter system of claim 1 wherein the polymeric material has a Shore durometer hardness of about 60A to about 65D.

6. The catheter system of claim 1 wherein the balloon is formed of elastomeric material.

7. The intravascular catheter system of claim 6 wherein the balloon is formed of an elastomeric material selected from the group consisting of latex, silicone, polyurethane, polyolefin elastomer, flexible polyvinyl chloride, ethylene vinyl acetate, ethylene methylacrylate, ethylene ethylacrylate, styrene butadiene styrene, and ethylene propylene diene rubber.

8. The intravascular catheter system of claim 1 wherein the balloon is formed of a thermoplastic aromatic polyether polyurethane.

9. The intravascular catheter system of claim 8 wherein the balloon has a hoop strength of about 10,000 psi to about 20,000 psi.

10. The intravascular catheter system of claim 1 wherein the balloon has a substantially elastic expansion when pressurized within a working pressure range of the balloon.

11. The intravascular catheter system of claim 1 wherein the balloon has a substantially elastic recoil after being expanded to implant the stent in the body, so that the balloon has a substantially wingless deflation configuration.

12. A catheter system for implanting a stent in a patient's body, comprising:
   a) a catheter having an elongated shaft with proximal and distal ends and an inflation lumen extending within at least a portion of a distal shaft section to a location spaced proximally from the distal end;
   b) an essentially wingless radially expansive uninflated compliant balloon formed of an elastomeric material selected from the group consisting of latex, silicone, polyurethane, ethylene alpha olefin polymer, flexible polyvinyl chloride, ethylene methylacrylate, ethylene ethylacrylate, styrene butadiene styrene, and ethylene propylene diene rubber, mounted on the distal section of the catheter shaft, with an interior chamber in fluid communication with the inflation lumen; and
   c) an expandable stent disposed about and mounted onto the essentially wingless uninflated balloon so that radial expansion of the balloon expands the stent mounted thereon and implants the stent in the body.

13. The catheter system of claim 12 wherein the elastomeric material comprises a thermoplastic polyether polyurethane polymer.

14. A method of implanting a stent within a patient's body, comprising:
   a) providing a catheter system for implanting a stent in a patient's body, comprising:
      i) a catheter having an elongated shaft with proximal and distal ends and an inflation lumen extending within at least a distal shaft section to a location spaced proximally from the distal end;
      ii) an essentially wingless radially expansive uninflated compliant balloon formed of polymeric material, mounted on the distal section of the catheter shaft, with an interior chamber in fluid communication with the inflation lumen; and
      iii) an expandable stent disposed about and mounted onto the essentially wingless uninflated balloon so that radial expansion of the balloon expands the stent mounted thereon and implants the stent in the body;
   b) inserting the catheter system into the patient's body; and c) inflating the balloon to produce radial expansion of the balloon and the stent mounted thereon.

15. The method the claim 14 further including advancing the catheter system to a desired region within a lumen of the patient's body.

16. The method of claim 14 further including radially expanding the balloon by delivering inflation fluid through the inflation lumen to the balloon interior chamber.

17. The method the claim 14 wherein the polymeric material is a thermoplastic aromatic polyether polyurethane, and including deflating the balloon to a preinflation radial and axial size.

18. The method of claim 14 including after (c), deflating the balloon to radially retract the balloon to an essentially wingless shape, and removing the catheter from the patient's body, with the stent remaining within the patient's body.

19. The method of claim 14 wherein the uninflated balloon has a preinflation radial and axial size, and including after (c), deflating the balloon to a substantially preinflation radial and axial size.

20. An intravascular catheter system for implanting a stent in a patient's body, comprising:
   a) a catheter having an elongated shaft with proximal and distal ends and an inflation lumen extending within at least a portion of a distal shaft section to a location spaced proximally from the distal end;
   b) a single layered, essentially wingless uninflated compliant balloon mounted on the distal section of the catheter shaft, with an interior chamber in fluid communication with the inflation lumen; and
   c) an expandable stent disposed about and mounted onto the single layered, essentially wingless uninflated compliant balloon so that radial expansion of the balloon expands the sten mounted thereon and implants the stent in the body.

21. The catheter of claim 20 wherein the balloon is formed of polymeric material selected from the group consisting of latex, silicone, polyurethane, ethylene alpha olefin polymer, flexible polyvinyl chloride, ethylene methylacrylate, ethylene ethylacrylate, styrene butadiene styrene, and ethylene propylene diene rubber.

22. A method of implanting a stent within a patient's body, comprising:
   a) providing a catheter system for implanting a stent in a patient's body, comprising:
      i) a catheter having an elongated shaft with proximal and distal ends and an inflation lumen extending within at least a distal shaft section to a location spaced proximally from the distal end;
      ii) a single layered, essentially wingless uninflated compliant balloon mounted on the distal section of the catheter shaft, with an interior chamber in fluid communication with the inflation lumen; and
      iii) an expandable stent disposed about and mounted onto the single layered, essentially wingless uninflated compliant balloon so that radial expansion of the balloon expands the stent mounted thereon and implants the stent in the body;
   b) inserting the catheter system into the patient's body; and
   c) inflating the balloon to produce radial expansion of the balloon and the stent mounted thereon.

* * * * *